United States Patent
Benade et al.

(10) Patent No.: US 11,826,450 B2
(45) Date of Patent: Nov. 28, 2023

(54) COSMETIC COMPOSITIONS

(71) Applicant: KAO Corporation S.A., Barbera del Valles (ES)

(72) Inventors: Juergen Benade, Emmerich (DE); Pilar Castan Barberan, Barbera del Valles (ES); Nuria Marimon Margarit, Barbera del Valles (ES); Reinout Van Der Veen, Emmerich (DE)

(73) Assignee: KAO Corporation S.A., Barbera del Valles (ES)

( * ) Notice: Subject to any disclaimer, the term of this patent is extended or adjusted under 35 U.S.C. 154(b) by 209 days.

(21) Appl. No.: 17/047,751

(22) PCT Filed: Apr. 16, 2019

(86) PCT No.: PCT/EP2019/059786
§ 371 (c)(1),
(2) Date: Oct. 15, 2020

(87) PCT Pub. No.: WO2019/201906
PCT Pub. Date: Oct. 24, 2019

(65) Prior Publication Data
US 2021/0154113 A1    May 27, 2021

(30) Foreign Application Priority Data

Apr. 16, 2018   (EP) .................... 18382255

(51) Int. Cl.
| | |
|---|---|
| *A61K 8/37* | (2006.01) |
| *A61K 8/04* | (2006.01) |
| *A61K 8/34* | (2006.01) |
| *A61K 8/365* | (2006.01) |
| *A61Q 5/02* | (2006.01) |
| *A61Q 5/10* | (2006.01) |
| *A61Q 9/02* | (2006.01) |
| *A61Q 19/10* | (2006.01) |

(52) U.S. Cl.
CPC ............. *A61K 8/37* (2013.01); *A61K 8/046* (2013.01); *A61K 8/345* (2013.01); *A61K 8/365* (2013.01); *A61Q 5/02* (2013.01); *A61Q 5/10* (2013.01); *A61Q 9/02* (2013.01); *A61Q 19/10* (2013.01)

(58) Field of Classification Search
None
See application file for complete search history.

(56) References Cited

U.S. PATENT DOCUMENTS

| | | |
|---|---|---|
| 3,992,443 A | 11/1976 | Springmann |
| 4,625,057 A | 11/1986 | Springmann et al. |
| 7,179,452 B2 | 2/2007 | Müller et al. |
| 2005/0197261 A1 | 9/2005 | Leinweber et al. |
| 2009/0023623 A1 | 1/2009 | Yamamoto et al. |
| 2011/0034359 A1 | 2/2011 | Rabbat et al. |
| 2014/0315769 A1 | 10/2014 | Rabbat et al. |
| 2015/0011455 A1 | 1/2015 | Moragas Arjant et al. |
| 2017/0009172 A1 | 1/2017 | Bender et al. |

FOREIGN PATENT DOCUMENTS

| | | |
|---|---|---|
| JP | 03-103500 | 4/1991 |
| WO | 2009040370 | 4/2009 |
| WO | 2016093291 | 6/2016 |

OTHER PUBLICATIONS

Shigabieva Yu. A. Kolloidno-khimicheskie svoystva penoobrazuyushchikh i gelevykh kompozitsiy s biologicheski aktivnymi komponentami (Colloidal and Chemical Properties of Foaming and Gel Compositions with Biologically Active Components): a thesis . . . of the candidate of chemical sciences: 02.00.11—Kazan, 2014.—158 p., pp. 8, 10, 113, chapter 1.3.

Notice of Reasons for Rejection in corresponding Japanese Patent Application Serial No. 2020-556901, dated Feb. 13, 2023 (English translation attached).

*Primary Examiner* — Nicole P Babson

(74) *Attorney, Agent, or Firm* — Hovey Williams LLP

(57) ABSTRACT

A cosmetic composition comprising one or more ether carboxylic acids and one or more non-ionic surfactants, method for the preparation of the cosmetic composition, and method for use of the cosmetic composition for the cleansing of skin and/or hair.

13 Claims, No Drawings

COSMETIC COMPOSITIONS

FIELD OF THE INVENTION

The present invention relates to a cosmetic composition comprising one or more ether carboxylic acids and one or more non-ionic surfactants. The present invention also relates to the methods of making and using the cosmetic composition.

STATE OF THE ART

Skin and hair cleanser compositions are required to have not only good detergency and cleansing ability, but they also need to be mild and be well tolerated by the skin and do not cause excessive defatting or dryness to the skin and hair, to be of easy applicability, homogeneous and flowable at room temperature. In addition, skin and hair cleanser compositions are demanded by consumers to exhibit good foaming properties.

In order that the composition meets all those requirements and is useful for the cleaning of hair and skin, it has to share at least the following features:

Foam ability to obtain a high volume of foam, and wherein the foam is obtained in a short period of time;

Foam stability, which is the foam remaining after a certain period at rest;

Foam quantity, associated with good cleaning effect;

Foam quality: in a number of surfactant applications, consumers are looking for good quality foam. For example, a hair or skin cleanser that does not produce enough creamy, stable foam during its application will not be considered as adequate by consumers. Thus, foam quality, associated to the creaminess of the foam (connected with conditioning effect), the size of the foam and the consistency of the foam, related to the firmness or thickness of the foam, is a major feature to be fulfilled.

It is a technically complex challenge to prepare suitable formulations meeting the above described requirements, as the number of surfactant combinations that meet the requirement profile tends to be small. Traditionally, anionic surfactants have been used for skin and hair cleansing compositions suitable to generate a foaming cosmetic composition.

EP2612652A1 describes a cleansing composition comprising an ether carboxylic acid or a salt thereof having an alkyl chain containing two or more alkyl groups, and a specific distribution of moles of ethylene oxide. It describes good foaming properties, volume of foam and rinsing properties.

The combination of anionic surfactants such as ether carboxylic acids and alkyl ether sulphates is also described. EP1994922A1 describes the combination of polyoxyethylene alkylether sulphate, an ether carboxylic acid surfactant, an alkyl polyglucoside and one or more higher fatty acid and a higher alcohol to obtain skin cleansing compositions with good foam properties.

Another approach is the provision of surfactant formulations with additives, so-called foam boosters or foam-enhancing agents, which favourably influence the foam properties of the mixtures. EP1479754 describes surfactant mixtures containing alkyl ether carboxylates and ether glycerides as foam booster for surfactant mixtures.

Another possibility to enhance the foamability and the quality of foam is the incorporation of a polymer in the cleansing composition. For example, EP1329214A1 describes a hair cleansing composition comprising an anionic surfactant having a sulphate group, a higher alcohol and a cationic polymer with good foamability and lubricity foam quality upon rinsing.

From the state of the art set forth above, it can be seen that there is still a need for better compositions. Thus, it is an object of the present invention to provide a cosmetic composition being mild, with easy applicability, with good detergency and cleansing ability, flowable and homogeneous at room temperature and exhibiting good foaming properties such as foam ability, foam stability, foam quantity and foam quality; wherein the cosmetic composition comprises an ether carboxylic acid and a non-ionic surfactant in certain ratios. Another object of the present invention is a method to prepare a cosmetic composition by mixing the ingredients with water and stirring to obtain a homogeneous solution, and the use of such cosmetic composition for the cleansing of skin and/or hair.

SUMMARY OF THE INVENTION

The first object of the present invention is a cosmetic composition, said composition comprising:
(a) One or more ether carboxylic acid or cosmetically acceptable salt thereof of formula (I)

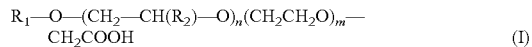

$$R_1-O-(CH_2-CH(R_2)-O)_n(CH_2CH_2O)_m-CH_2COOH \quad (I)$$

wherein $R_1$ is a linear or branched alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, n and m are independently an integer number from 0 to 15, and wherein the sum of m+n is from 1 to 15; and
(b) One or more non-ionic surfactant, Wherein the malar ratio between the component (a) and the component (b) is within a range from 8:1 to 2:1, The second object of the present invention is a cosmetic composition, said composition comprising:
(a) One or more ether carboxylic acid or cosmetically acceptable salt thereof of formula (I)

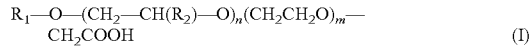

$$R_1-O-(CH_2-CH(R_2)-O)_n(CH_2CH_2O)_m-CH_2COOH \quad (I)$$

wherein $R_1$ is a linear or branched alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, n and m are independently an integer number from 0 to 15, and wherein the sum of m+n is from 1 to 15; and
(b) One or more non-ionic surfactant Wherein the molar ratio between the component (a) and the component (b) is within a range from 8:1 to 2:1, and wherein the composition is obtainable by a process comprising at least the following steps:
i. Alkoxylating a fatty alcohol;
ii. Carboxymethylating the mixture obtained in step i)
iii. Hydrolysis of the ether carboxylic acid ester formed as by-product during step ii) by saponification reaction.

According to the third aspect, the present invention provides a method for the prepare ion of the cosmetic composition of the invention.

In the fourth aspect, the present invention relates to the use of a cosmetic composition according to the invention for the cleansing of skin and/or hair.

According to the fifth aspect, the present invention provides a method for the cleansing of skin and/or hair, comprising the steps of wetting or dampening the skin and/or hair, applying a sufficient amount of composition according to the invention on the skin and/or hair, and rinsing the skin and/or hair with water.

DETAILED DESCRIPTION OF THE INVENTION

All percentages are weight percentages, unless otherwise indicated. Active weight is the weight of the active matter with respect to the total weight of the active material of the composition, wherein by active matter it is understood the set of specific components responsible for a certain action. In the scope of the present application (i.e. with reference to the composition) the active matter is the totality of ingredients, from which are derived all or part of its effectiveness.

As cosmetic composition it is understood a composition suitable as an ingredient to be used in cosmetic and personal care applications.

The main object of the present invention is a cosmetic, composition comprising:
 (a) One or more ether carboxylic acid or cosmetically acceptable salt thereof of formula (I)

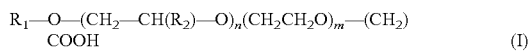
(I)

wherein $R_1$ is a linear or branched alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, n and m are independently an integer number from 0 to 15, and wherein the sum of m+n is from 1 to 15; and
 (b) One or more non-ionic surfactant, Wherein the molar ratio between the component (a) and (b) is from 8:1 to 2:1, preferably from 7:1 to 3:1, more preferably from 6:1 to 4:1

Ether Carboxylic Acid or Salt Thereof (a):

The present invention comprises one or more ether carboxylic acid or cosmetically acceptable salt thereof (a) represented by formula (I)

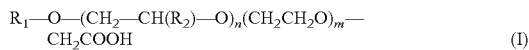
(I)

wherein $R_1$ is a linear or branched alkyl or alkenyl chain having from 4 to 22 carbon atoms, preferably from 10 to 16 carbon atoms, more preferably from 12 to 16 carbon atoms; $R_2$ is a $C_1$-$C_3$ linear or branched alkyl chain, n and m are independently an integer number from 0 to 15, and wherein the sum of m+n is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3.

In one embodiment of the present invention, the ether carboxylic acids or salts thereof can be ethoxylated and propoxylated, the value of n and of m in formula (I) therefore being greater than 0 and $R_2$ being methyl. The order of sequence of the ethylene oxide and propylene oxide groups is not critical for the invention. Therefore, both the ether carboxylic acid or salt thereof according to formula (I) containing ethylene oxide and propylene oxide in separate blocks and those ether carboxylic acids or salts thereof according to formula (I) where ethylene oxide and propylene oxide are randomly distributed can be used in the cosmetic compositions according to the invention.

In a preferred embodiment of the present invention, the ether carboxylic acid or salts thereof represented by formula (I) are free of propylene oxide, i.e. n=0.

In another embodiment of the present invention, $R_1$ is a linear or branched alkyl containing 4 to 22 carbon atoms or a linear alkenyl group containing 4 to 22 carbon atoms and from 1 to 3 double bonds; preferably the alkyl or alkenyl contains 10 to 18 carbon atoms, more preferably 12 to 16 carbon atoms.

In another embodiment of the present invention. $R_1$ is a linear or branched alkyl or a linear alkenyl derived from natural fats and oils. Preferred fats and oils include palm oil, coconut oil, sunflower oil, rapeseed oil, castor oil, olive oil, soybean oil; animal fat such as tallow, fish oil, hardened oils and semihardened oils thereof, and mixtures thereof. In a preferred embodiment. $R_1$ is a linear or branched alkyl or a linear alkenyl derived from palm oil or coconut oil.

As used herein, the term "alkyl" refers to a straight or branched hydrocarbon chain containing from 4 to 22 carbon atoms.

As used herein, the term "alkenyl" refers to a linear hydrocarbon chain containing from 4 to 22 carbon atoms and from 1 to 3 double bonds.

Cosmetically acceptable salts of ether carboxylic acid represented by formula (I) are salts of alkali metal or alkaline earth metal ions, such as sodium, potassium, magnesium or calcium, ammonium, alkylammonium, alkanolammonium or glucammonium salts. In a preferred embodiment of the present invention, salts of ether carboxylic acid represented by formula (I) are sodium salt or potassium salt of ether carboxylic acid.

Preparation Process

The ether carboxylic acid or salts thereof (a) according to the invention can be prepared by a process including at least the steps of the alkoxylation of a fatty alcohol to obtain a mixture comprising alkoxylated fatty alcohols, and the alkylation of the mixture with a halocarboxylic acid.

i) Alkoxylation of Fatty Alcohol:

The alkoxylation of alcohols can be carried out under standard conditions known by persons skilled in the art. For example, the polyoxyethylene group is obtained by the addition of ethylene oxide to fatty alcohols, mostly with an alkaline catalyst such as NaOH, KOH or NaOCH$_3$, giving a broad polyoxyethylene oxide distribution (broad ethoxylation degree). For special applications the ethoxylation can be catalysed by Lewis acids or by using metallic Na or NaH to achieve a narrow range distribution (narrow ethoxylation degree). However, one may also start from commercially available ethoxylated alcohols.

The product resulting from the alkoxylation reaction comprises a mixture of alkoxylated fatty alcohol and non-alkoxylated fatty alcohol.

In an embodiment of the present invention, the alkoxylated fatty alcohol is represented by formula (II):

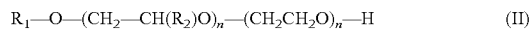
(II)

wherein $R_1$ is a linear or branched alkyl chain, having from 4 to 22 carbon atoms, preferably from 10 to 18 carbon atoms, more preferably from 12 to 16 carbon atoms; $R_2$ is a $C_1$-$C_3$ linear or branched alkyl chain, m and n are independently an integer number from 0 to 15, and wherein the sum of m n is, from 1 to 15, preferably n and m are independently an integer number from 0 to 10, and wherein the sum of m n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3.

Suitable fatty alcohols according to formula (II) are n-butanol, n-hexanol, n-octanol, 2-ethylbutanol, 2-methylpentanol, 2-ethylhexanol, 2-methylheptanol, n-decanol, 2-methyl-4-nonanol, 3,7-dimethyl-3-octanol, 3,7-dimethyl-1-octanol, 3,6-dimethyl-3-octanol, lauryl alcohol (1-dodecanol), myristyl alcohol (1-tetradecanol), cetyl alcohol (1-hexadecanol), palmitoleyl alcohol (cis-9-hexadecan-1-ol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), ricinoleyl alcohol (12-hydroxy-9-octadecen-1-ol), arachidyl alcohol (1-eicosanol), behenyl alcohol (1-docosanol), erucyl alcohol (cis-13-docosen-1-ol) or mixtures thereof.

In an embodiment of the present invention, the fatty alcohol is lauryl alcohol, myristyl alcohol (1-tetradecanol), the corresponding alkoxylated alcohols thereof or mixtures thereof.

In another embodiment of the present invention, fatty alcohols are derived from natural fats and oils. Preferred fats and oils include palm oil, coconut oil, sunflower oil, rapeseed oil, castor oil, olive oil, soybean oil; animal fat such as tallow, fish oil, hardened oils and semihardened oils thereof, and mixtures thereof. As a result of their natural origin, the alcohols that are alcoxylated may contain a great variety of alkyl and alkenyl groups, said groups being linear or branched, saturated or unsaturated.

In another embodiment of the present invention, the proportion of fatty alcohols wherein $R_1$ is $C_{12}$ or $C_{14}$ is higher than 60% wt., preferably higher than 80% wt.

ii) Carboxymethylation Reaction:

The carboxymethylation of the mixture of alkoxylated fatty alcohols and non-alkoxylated fatty alcohols obtained in step i) can be conducted in several ways but one known way is as described for example in EP2807241A1.

In such case the mixture of alkoxylated alcohols and non-alkoxylated alcohols is reacted with a strong base, like sodium or potassium hydroxide, in the conditions known by the person skilled in the art, which include possibly in the presence of a reducing agent, e.g. sodium borohydride, to obtain the corresponding alkoxylates. One possible way is the carboxymethylation with sodium monochloroacetate (SOMA).

According to the described procedure, after the carboxymethylation the alkali metal ethercarboxylate may be converted to the free ether carboxylic acid by acidification with any acid, preferably HCl and posterior removal of aqueous phase.

The composition that results from the carboxymethylation reaction comprises ether carboxylic acid, free fatty alcohol, free alkoxylated fatty alcohol and the ester obtained as a by-product from the reaction of ether carboxylic acid and free fatty alcohol and free alkoxylated alcohol present in the reaction mixture.

Non-Ionic Surfactant (b):

The present invention comprises a non-ionic surfactant (b). The general definition and general properties of non-ionic surfactants are well-known by the skilled in the art. The definition in "NONIONIC SURFACTANTS—Chemical Analysis" ISBN 0-8247-7626-7 is incorporated herein by reference.

Examples of non-ionic surfactants according to the invention include non-ionic surfactants like alkanolamides, alkoxylated alkanolamides, alkoxylated trimethyolol propane, alkoxylated 1,2,3-trihydroxy hexane, alkoxylated pentaetrythritol, alkoxylated sorbitol, alkoxylated glycerol fatty acid partial ester, alkoxylated trimethyolol propane fatty acid ester, alkoxylated 1,2,3-trihydroxy hexane fatty acid ester, alkoxylated pentaetrythritol fatty acid ester, alkoxylated sorbitol fatty acid ester, fatty alcohol, fatty alcohol polyglycol ethers, alkylphenol, alkylphenol polyglycol ethers, fatty acid polyglycol esters, fatty acid amide polyglycol ethers, fatty amine polyglycol ethers, mixed ethers and mixed formals, optionally partly oxidized alk(en)yl oligoglycosides or glucuronic acid derivatives, fatty acid-N-alkylglucamides, ethoxylated glutamine derivatives, protein hydrolyzates (particularly wheat-based vegetable products), polyol fatty acid esters, sugar esters, alkyl polyglucosides sorbitan esters and polysorbates.

In an embodiment of the invention, the non-ionic surfactant (b) is a fatty alcohol containing from 4 to 22 carbon atoms, wherein the fatty alcohol may be ethoxylated and/or propoxylated.

The C4-C22 fatty alcohols are aliphatic alcohols derived from natural fats and oils, as well as synthetic origin. Preferred fats and oils include palm oil, coconut oil, sunflower oil, rapeseed oil, castor oil, olive oil, soybean oil; and animal fat such as tallow, bone oil; fish oil, hardened oils and semi hardened oils thereof; and mixtures thereof.

Optionally, the C4-C22 fatty alcohols are ethoxylated and/or propoxylated, having an average alkoxylation degree from 1 to 15, preferably from 1 to 10, more preferably from 1 to 6, most preferred from 1 to 3.

Examples of C4-C22 fatty alcohols include capryl alcohol (1-octanol), pelargonic alcohol (1-nonanol), capric alcohol (1-decanol), lauryl alcohol (1-dodecancil), myristyl alcohol (1-tetradecanol), cetyl alcohol (1-hexadecanol), palmitoleyl alcohol (cis-9-hexadecan-1-ol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol(9Z,12Z,15Z-octadecatrien-1-ol), elaidolinolenyl alcohol (9E, 12E, 15-E-octadecatrien-1-ol), ricinoleyl alcohol (12-hydroxy-9-octadecen-1-ol), arachidyl alcohol(1-eicosanol), behenyl alcohol (1-docosanol), erucyl alcohol (cis-13-docosen-1-ol, and mixtures thereof.

Examples of commercially available fatty alcohols are those corresponding to the commercial reference KALCOL® 6098, (INCI Cetyl Alcohol, KALCOL® 2466 (INCI C12-C16 Alcohol), KALCOL® 8098 (INCI Stearyl Alcohol), KALCOL® 8850P, (INCI Cetearyl Alcohol), all of them marketed b KAO Chemicals Europe.

In a preferred embodiment the non-ionic surfactant b) of the composition according to the invention comprises one or more fatty alcohols of Formula (II):

$$R_3—O—(CH_2—CH(R_4)O)_p—(CH_2CH_2O)_q—H \quad \text{(III)}$$

wherein R is a linear or branched alkyl chain, having from 4 to 22 carbon atoms, preferably from 10 to 18 carbon atoms, more preferably from 12 to 16 carbon atoms; $R_4$ is a $C_1$-$C_3$ linear or branched alkyl chain, p and q are are independently an integer number from 0 to 15, and wherein the sum of p+q is from 0 to 15, preferably p and q are independently an integer number from 0 to 10, and wherein the sum of p+q is from 0 to 10, more preferably p and q are independently an integer number from 0 to 6, and wherein the sum of p+q is from 0 to 6, even more preferably p and q are independently an integer number from 0 to 3, and wherein the sum of p+q is from 0 to 3.

In a preferred embodiment of the present invention, p is 0.

In another preferred embodiment of the present invention, the non-ionic surfactant (b) of the composition comprises a mixture of fatty alcohols of formula (II) wherein the sum of p+q is 0 and alkoxylated fatty alcohols of formula (II) wherein the sum of p+q is from to 15, preferably from 1 to 10, more preferably from 1 to, even more preferably from 1 to 3.

Examples of $C_4$-$C_{22}$ fatty alcohols include capryl alcohol (1-octanol), pelargonic alcohol (1-nonanol), capric alcohol (1-decanol), lauryl alcohol (1-dodecanol), myristyl alcohol (1-tetradecanol), cetyl alcohol (1-hexadecanol), palmitoleyl alcohol (cis-9-hexadecan-1-ol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol(9Z,12Z,15Z-octadecatrien-1-ol), elaidolinolenyl alcohol (9E, 12E, 15-E-octadecatrien-1-ol), ricinoleyl alcohol (12-hydroxy-9-octadecen-1-ol), arachidyl alcohol(1-eicosanol), behenyl alcohol (1-docosanol), erucyl alcohol (cis-13-docosen-1-ol, and mixtures thereof.

In an embodiment of the present invention, the non-ionic surfactant (b) corresponds to the non-carboxymethylated species from the obtention of the ether carboxylic acid (a). In another embodiment of the present invention, the non-ionic surfactant (b) comprising one or more fatty alcohols of Formula (II) corresponds to the non-carboxymethylated species (alkoxylated fatty alcohol and non-alkoxylated fatty alcohol) from the obtention of the ether carboxylic acid (a).

In another embodiment of the present invention, the non-ionic surfactant (b) comprising one or more fatty alcohols of Formula (III) is added to the cosmetic composition as a blend or mixture.

Amphoteric Surfactant (c):

The cosmetic composition of the present invention optionally comprises a component (c), said component being an amphoteric surfactant.

Examples of amphoteric surfactant are alkyl amine oxides, alkyl betaines, alkyl sulphobetaines (sultaines), amidoalkyl betaines, alkyl glycinates, alkyl carboxyglycinates, alkyl amphoacetates, alkyl amphopropionates, alklylamphoglycinates, alkyl amidopropyl betaines, alkyl amidopropyl- and hydroxysultaines. Particularly preferred amphoteric surfactants are betaines, alkyl amine oxides, alkylamphoglycinates and alkyl amphoacetates, In a preferred embodiment of the present invention, the component (c) comprises one or more ampholytes. Specific examples of ampholytes are amine oxides. Suitable amine oxides according to the present invention are amine oxides with a hydrocarbon chain containing between 8 and 18 carbon atoms. Examples of commercially available amine oxides are those with the commercial reference OXIDET® DM-20 (INCI name Lauramine Oxide), OXIDET® DMCLD (INCI name Cocamine Oxide) OXIDET® DM-246 (INCI name Cocamine Oxide), OXIDET® DM-4 (INCI name Myristamine Oxide), OXIDET® L-75 (INCI name Cocamidopropylamine Oxide), all of them marketed by KAO Chemicals Europe.

In a most preferred embodiment of the present invention, the component (c) comprises one or more betaines. Specific examples of betaines are alkyl betaines, alkyl sulphobetaines (sultaines), amidoalkyl betaines, alkyl glycinates, alkyl carboxyglycinates, alkyl amphoacetates, alkyl amphopropionates alkylamphoglycinates, alkyl amidopropyl betaines and hydroxysultaines. Particularly preferred betaines are alkyl amidopropyl betaines, alkyl amidopropyl hydroxysultaines, alkyl hydroxysultaines and alkyl amphoacetates. In a preferred embodiment the betaines are alkyl amidopropyl betaines.

Examples of commercially available useful betaine surfactants according to the invention are BETADET® HR, BETADET® HR-50K, BETADET® S-20, BETADET® SHR and BETADET® THC-2, all marketed by Kao Chemicals Europe.

Ether Carboxylic Acid Ester (d):

The cosmetic composition of the present invention optionally may comprise an ether carboxylic acid ester (d) of formula (IV)

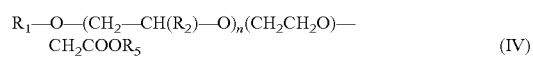

$$R_1\text{—O—}(CH_2\text{—}CH(R_2)\text{—O})_n(CH_2CH_2O)\text{—}CH_2COOR_5 \quad (IV)$$

Wherein $R_1$ is an alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, $R_5$ is an alkyl or alkenyl chain, having from 4 to 22 carbon atoms, preferably from 10 to 18 carbon atoms, more preferably from 12 to 16 carbon atom, or —$(CH_2\text{—}CH(R_2)\text{—O})_p(CH_2CH_2O)_q\text{—}R_3$; wherein $R_3$ is an alkyl or alkenyl chain, having from 4 to 22 carbon atoms, preferably from 10 to 18 carbon atoms, more preferably from 12 to 16 carbon atoms, n and m are independently an integer number from 0 to 15, the sum of n+m is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3; p and q are independently an integer number from 0 to 15, the sum of p+q is from 0 to 15, preferably p and q are independently an integer number from 0 to 10, and wherein the sum of p+q is from 0 to 10, more preferably p and q are independently an integer number from 0 to 6, and wherein the sum of p+q is from 0 to 6, even more preferably p and q are independently an integer number from 0 to 3, and wherein the sum of p+q, is from 0 to 3.

In an embodiment of the present invention, the sum of p+q is 0.

In another embodiment of the present invention, the sum of p+q is from 1 to 15, preferably from 1 to 10, more preferably from 1 to 6, even more preferably from 1 to 3.

In an embodiment of the present invention, the amount of ether carboxylic acid ester (d) is lower than 20% wt. with respect to the total active weight of the sum of (a), (b) and (d), preferably lower than 10% wt. with respect to the total active weight of the sum of (a), (b) and (d).

In an embodiment of the present invention, the ether carboxylic acid ester may be obtained as a by-product from the reaction of ether carboxylic acid (a) and free fatty alcohol and free alkoxylated alcohol present in the reaction mixture.

In an embodiment of the present invention, the ether carboxylic acid ester (d) is obtained by the reaction from the ether carboxylic acid (a) and free non-ionic surfactant (b) present in the cosmetic composition.

In an embodiment of the present invention, the ether carboxylic acid ester (d) can be hydrolysed by means of a saponification reaction.

Saponification Reaction

The saponification reaction can be conducted by the reaction of an alkali with the ether carboxylic acid ester to, through hydrolysis of the ester, obtain the corresponding alcohol and ether carboxylic acid.

In an embodiment of the invention, the alkali is an alkali hydroxide, such as NaOH or KOH. Preferably, the alkali hydroxide is KOH.

In an embodiment of the present invention, the molar ratio between the ether carboxylic acid (a) and KOH is from 1:1 to 1.23, preferably from 1:1 to 1:1.17

In an embodiment of the present invention, after the saponification reaction, the amount of ether carboxylic acid ester (d) is lower than 15% wt, with respect to the total active weight of the sum of (a), (b) and (d), preferably lower than 10% wt. with respect to the total active weight of the sum of (a), (b) and (d).

In another embodiment of the present invention, there is an essential absence of ether carboxylic acid ester (d). By essential absence of ether carboxylic acid ester (d) it is understood that the amount of ether carboxylic acid ester (d) is lower than 2% wt, such as lower 1% wt, e.g. lower than 0.5% wt. with respect to the total active weight of the sum of (a), (b) and (d).

Electrolyte (e)

The cosmetic composition of the present invention optionally comprises a component (e), said component being an electrolyte.

The electrolyte is preferably a mono-, di- or trivalent metal salt, and more particularly alkaline and alkaline-earth metal salts such as barium, calcium, sodium, potassium, magnesium salts and mixtures thereof. The ions constituting these salts may be chosen from carbonates, bicarbonates, sulfates, phosphates, sultanates, glycerophosphates, borates, bromides, chlorides, nitrates, acetates, hydroxides.

Preferred electrolytes are magnesium chloride, potassium chloride, sodium chloride, calcium chloride, magnesium bromide, magnesium sulphate or magnesium chloride Even more preferably, electrolytes are sodium chloride and potassium chloride.

Cosmetic Composition of the Invention

The main object of the present invention is a cosmetic composition comprising:

(a) one or more ether carboxylic acid or cosmetically acceptable salt thereof of formula (I)

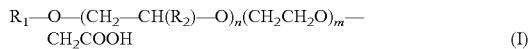

$R_1$—O—$(CH_2$—$CH(R_2)$—O$)_n(CH_2CH_2O)_m$— $CH_2COOH$ (I)

wherein $R_1$ is a linear or branched alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, n and m are independently an integer number from 0 to 15, and wherein the sum of m+n is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3.

(b) one or more on-ionic surfactants.

Wherein the molar ratio between the component (a) and (b) is from 8:1 to 2:1 preferably from 7.1 to 3.1, more preferably between 6:1 to 4:1.

In another embodiment of the present invention, the cosmetic composition comprises:

(a) one or more ether carboxylic acid or cosmetically acceptable salt thereof of formula (I)

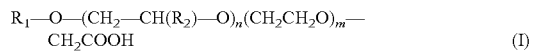

$R_1$—O—$(CH_2$—$CH(R_2)$—O$)_n(CH_2CH_2O)_m$— $CH_2COOH$ (I)

wherein R is a linear or branched alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, n and m are independently an integer number from 0 to 15, and wherein the sum of m+n is from 1 to 15, preferably n and m are independently an integer number from 0 to 10, and wherein the sum of m+n is from 1 to 10, more preferably and m are independently an integer number from 0 to 6, and wherein the sum of in +n is from 1 to 6, even more preferably n and m are independently an integer number from 0 to 3, and wherein the sum of m+n is from 1 to 3.

(b) one or more non-ionic surfactants, wherein the non-ionic surfactant comprises a fatty alcohol of formula (III)

$R_3$—O—$(CH_2$—$CH(R_4)O)_p(CH_2CH_2O)_q$—H (III)

wherein $R_3$ is a linear or branched alkyl chain, having from 4 to 22 carbon atoms, preferably from 10 to 18 carbon atoms, more preferably from 12 to 16 carbon atoms; $R_4$ is a C1-C3 linear or branched alkyl chain, p and q are independently an integer number from 0 to 15, and wherein the sum of p+q is from 0 to 15, preferably p and q are independently an integer number from 0 to 10, and wherein the sum of p+q is from 0 to 10, more preferably, p and q are independently an integer number from 0 to 6, and wherein the sum of p+q is from 0 to 6, even more preferably p and q are independently an integer number from 0 to 3, and wherein the sum of p+q is from 0 to 3;

and wherein the molar ratio between the component (a) and (b) is from 8:1 to 2:1, preferably from 7:1 to 3:1, preferably from 6:1 to 4:1, even more preferably from 5.5:1 to 4.5:1.

In an embodiment of the present invention, the non-ionic surfactant comprises a mixture of fatty alcohol of formula (III) wherein the sum of p+q is 0 and fatty alcohol of formula (III) wherein the sum of p+q is from 1 to 15, preferably from 1 to 10, more preferably from 1 to 6, even more preferably from 1 to 3.

In an embodiment of the present invention, the cosmetic composition comprises at least (a) one or more ether carboxylic acid of formula (I) and at least (b) a non-ionic surfactant, wherein the non-ionic surfactant (b) corresponds to the non-carboxymethylated species from the obtention of the ether carboxylic acid (a).

In an embodiment of the present invention, the cosmetic composition comprises at least (a) one or more ether carboxylic acid of formula (I) and at least (b) a non-ionic surfactant comprising one or more fatty alcohols of Formula (II), wherein the non-ionic surfactant (b) corresponds to the non-carboxymethylated species from the obtention of the ether carboxylic acid (a).

In another embodiment of the present invention, the cosmetic composition comprises at least (a) one or more ether carboxylic acid of formula (I) and at least (b) a non-ionic surfactant comprising one or more fatty alcohols of Formula (III), wherein the non-ionic surfactant is added to the cosmetic composition as a blend or mixture.

In an embodiment of the present invention, the percentage of active matter of the cosmetic composition comprising (a) an ether carboxylic acid or salt thereof of formula (I) and (b) a non-ionic surfactant is higher than 50%.

The active matter corresponds to the active matter weight-percent (wt %) calculated from the sum of active matter of all specific components responsible of a determined action. For the present invention, the active matter is for the surfactant components, that is (a), (b), (d) and optionally (c).

In another embodiment of the present invention, the cosmetic composition comprises:
(a) one or more ether carboxylic acid or cosmetically acceptable salt thereof of formula (I)

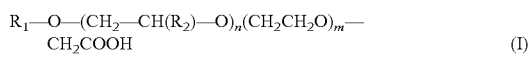

$$R_1-O-(CH_2-CH(R_2)-O)_n(CH_2CH_2O)_m-CH_2COOH \quad (I)$$

wherein $R_1$ is a linear or branched alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, n and m are independently an integer number from 0 to 15, and wherein the sum of m+n is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3;
(b) one or more non-ionic surfactant, wherein the non-ionic surfactant comprises a fatty alcohol;
(c) an amphoteric surfactant Wherein the molar ratio between the component (a) and (h) is from 8:1 to 2:1, preferably 7:1 to 3:1, more preferably between 6:1 to 4:1;

And wherein the molar ratio between component (a), component (b) and component (c) is 90:5:5 to 40:6:54, preferably from 70:5:25 to 45:7:48.

In another embodiment of the present invention, the cosmetic composition comprises:
(a) one or more ether carboxylic acid or cosmetically acceptable salt thereof of formula (I)

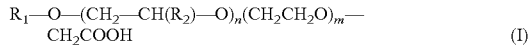

$$R_1-O-(CH_2-CH(R_2)-O)_n(CH_2CH_2O)_m-CH_2COOH \quad (I)$$

wherein $R_1$ is a linear or branched alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, n and m are independently an integer number from 0 to 15, and wherein the sum of m+n is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3;
(b) one or more non-ionic surfactant, wherein the non-ionic surfactant comprises a fatty alcohol;
(c) an amphoteric surfactant Wherein the molar ratio between the component (a) and (b) is from 8:1 to 2:1, preferably 7:1 to 3:1, more preferably between 6:1 to 4:1;

And wherein the molar ratio between component (a), component (b) and component (c) is 89:6:5 to 38:15:47, preferably from 82:8:10 to 60:10:30.

In another embodiment of the present invention, the cosmetic composition comprises:
(a) one or more ether carboxylic acid or cosmetically acceptable salt thereof of formula (I)

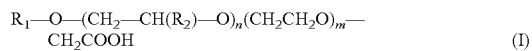

$$R_1-O-(CH_2-CH(R_2)-O)_n(CH_2CH_2O)_m-CH_2COOH \quad (I)$$

wherein $R_1$ is a linear or branched alkyl or alkenyl chain having from 4 to 22 carbon atoms, preferably from 10 to 18 carbon atoms, more preferably from 12 to 16 carbon atoms; $R_2$ is a linear or branched alkyl chain, n and m are independently an integer number from 0 to 15, and wherein the sum of m+n is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3;
(b) one or more non-ionic surfactant, wherein the non-ionic surfactant comprises a fatty alcohol;
(c) an amphoteric surfactant
(d) an ether carboxylic acid ester of formula (IV)

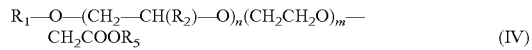

$$R_1-O-(CH_2-CH(R_2)-O)_n(CH_2CH_2O)_m-CH_2COOR_5 \quad (IV)$$

Wherein $R_1$ is an alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, $R_5$ is an alkyl or alkenyl chain, having from 4 to 22 carbon atoms, preferably from 10 to 18 carbon atoms, more preferably from 12 to 16 carbon atom, or $-(CH_2-CH(R_2)-O)_p(CH2CH2O)_q-R_3$; wherein $R_3$ is an alkyl or alkenyl chain, having from 4 to 22 carbon atoms, preferably from 10 to 18 carbon atoms, more preferably from 12 to 16 carbon atoms, n and m are independently an integer number from 0 to 15, the sum of n+m is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3, p and q are 0 or an integer number from 1 to 15, the sum of p+q is from 0 to 15, preferably p and q are independently an integer number from 0 to 10, and wherein the sum of p+q is from 0 to 10, more preferably p and q are independently an integer number from 0 to 6, and wherein the sum of p+q is from 0 to 6, even more preferably p and q are independently an integer number from 0 to 3, and wherein the sum of p+q is from 0 to 3; and wherein the molar ratio between the component (a) and (b) is from 8:1 to 2:1, preferably from 7:1 to 3:1, more preferably between 6:1 to 4:1.

In another embodiment of the present invention, the cosmetic composition comprises:
(a) one or more ether carboxylic acid or cosmetically acceptable salt thereof of formula (I)

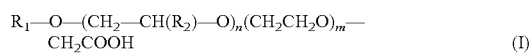

$$R_1-O-(CH_2-CH(R_2)-O)_n(CH_2CH_2O)_m-CH_2COOH \quad (I)$$

wherein $R_1$ is a linear or branched alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, n and mare independently an integer number from 0 to 15, and wherein the sum of m+n is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3;
  (b) one or more non-ionic surfactant, wherein the non-ionic surfactant comprises a fatty alcohol;
  (c) an amphoteric surfactant
  (d) an ether carboxylic acid ester of formula (IV)
  (e) an electrolyte
  Wherein the molar ratio between the component (a) and (b) is from 8:1 to 2:1, preferably from 7:1 to 3:1, more preferably between 6:1 to 4:1.

In another embodiment of the present invention, the cosmetic composition comprises:
  between 75% and 95%, preferably between 0% and 95% of component (a)
  between 5% and 20%, preferably between and 15% of component (b)
  each of the indicated amounts being expressed as percentage by weight of the mentioned component with respect to the total active weight of the sum of (a), (b) and (d).

In another embodiment of the present invention, the cosmetic composition comprises:
  between 27% and 90%, preferably between 35% and 85% of component (a)
  between 3% and 15%, preferably between 5% and 10% of component (b)
  between 5% and 70%, preferably between 10% and 60% of component (c)
  each of the indicated amounts being expressed as percentage by weight of the mentioned component with respect to the total active weight of the sum of (a), (b) and (c).

In another embodiment of the present invention, the cosmetic composition comprises:
  between 27% and 90%, preferably between 35% and 85% of component (a)
  between 3% and 15%, preferably between 5% and 10% of component (b)
  between 5% and 70%, preferably between 10% and 60% of component (c) component (d) in an amount lower than 15% wt, preferably in an amount lower than 10% wt.
  each of the indicated amounts being expressed as percentage by weight of the mentioned component with respect to the total active weight of the sum of (a), (b), (c) and (d).

In another embodiment of the present invention, the cosmetic composition comprises
  between 27% and 90%, preferably between 35% and 85% of component (a)
  between 3% and 15%, preferably between 5% and 10% of component (b)
  between 5% and 70%, preferably between 10% and 60% of component (c)
  each of the indicated amounts being expressed as percentage by weight of the mentioned component with respect to the total active weight of the sum of (a), (b) and (c); and in the absence of component (d)

In another embodiment of the present invention, the cosmetic composition comprises:
  between 27% and 90%, preferably between 35% and 85% of component (a)
  between 3% and 15%, preferably between 5% and 10% of component (b)
  between 5 and 70%, preferably between 10% and 60% of component (c) component (d) in an amount lower than 15% wt, preferably in an amount lower than 10%, or alternatively in the absence of component (d) component (e)
  each of the indicated amounts being expressed as percentage by weight of the mentioned component with respect to the total active weight of the sum of (a), (b), (c) and (d), and wherein the molar ratio between (a) and (e) is from 1:0.03 to 1:0.27, preferably from 1:0.04 to 1:0.16.

In another embodiment of the present invention, the cosmetic composition comprises:
  between 75% and 95%, preferably between 80% and 95% of component (a)
  between 5% and 20%, preferably between 5% and 15% of component (b) component (e)
  each of the indicated amounts being expressed as percentage by weight of the mentioned component with respect to the total active weight of the sum of (a) and (b); and wherein the molar ratio between (a) and (e) is from 1:0.03 to 1:0.27, preferably from 1:0.04 to 1:0.16.

In another embodiment of the present invention, the cosmetic composition comprises:
  (a) One or more ether carboxylic acid or cosmetically acceptable salt thereof of formula (I)

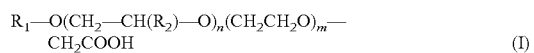
  (I)

wherein $R_1$ is an alkyl or alkenyl chain having from 4 to 22 carbon atoms, preferably from 10 to 18 carbon atoms, more preferably from 12 to 16 carbon atoms; $R_2$ is a C1-C3 linear or branched alkyl chain, n and m are independently an integer number from 0 to 15, and wherein the sum of m+n is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3;
  (b) a non-ionic surfactant, preferably a fatty alcohol;
  wherein the molar ratio between the component (a) and (b) is from 8:1 to 2:1, preferably from 7:1 to 3:1, more preferably from 6:1 to 4:1;
  and wherein the composition is obtainable by a process comprising at least the fallowing steps:
    i. Alkoxylating a fatty alcohol;
    ii. Carboxymethylating the mixture obtained in step i)
    iii. Hydrolysis of the ether carboxylic acid ester obtained as by-product during step ii) by a saponification reaction.

In an embodiment of the present invention, the cosmetic composition comprises (a) one or more ether carboxylic acid or salt thereof of formula (I), (b) a non-ionic surfactant, preferably a fatty alcohol, wherein the composition is obtainable by a process comprising at least the steps of i) alkoxylating a fatty alcohol, ii) carboxymethylating the mixture obtained in step i) and hydrolysis of the ether carboxylic acid ester obtained as by-product during step ii) by a saponification reaction, wherein the saponification reaction is done with KOH.

In another embodiment of the present invention, the cosmetic composition comprises:
  (a) One or more ether carboxylic acid or cosmetically acceptable salt thereof of formula (I)

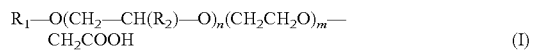
  (I)

wherein $R_1$ is an alkyl or alkenyl chain having from 4 to 22 carbon atoms, preferably from 10 to 18 carbon atoms, more preferably from 12 to 16 carbon atoms; $R_2$ is a $C_1$-$C_3$ linear or branched alkyl chain, n and m are independently an integer number from 0 to 15, and wherein the sum of m+m is from 1 to 15, preferably n and m are independently an integer number from 0 to 10, and wherein the sum of m+n is from 1 to 10, more preferably n and m are independently an integer number from 0 to 6, and wherein the sum of m+n is from 1 to 6, even more preferably n and m are independently an integer number from 0 to 3, and wherein the sum of m+n is from 1 to 3;

(b) a non-ionic surfactant, preferably a fatty alcohol;

wherein the molar ratio between the component (a) and (b) is from 8:1 to 2:1, preferably from 7:1 to 3:1, preferably from 6:1 to 4:1, even more preferably from 5.5:1 to 4.5:1;

and wherein the composition is obtainable by a process comprising at least the following steps:

i. Alkoxylating a fatty alcohol with an alkyl or alkenyl chain having from 4 to 22 carbon atoms, preferably from 10 to 18 carbon atoms, more preferably from 12 to 16 carbon atoms;

ii. Carboxymethylating the mixture obtained in step i) comprising at least an alkoxylated alcohol and alkoxides thereof with a C2 to C5 chlorocarboxylic acid;

iii. Converting the thus obtained ethercarboxylic acid salt to the free ethercarboxylic acid by addition of acid and subsequent phase separation;

iv. Hydrolysis of the ether carboxylic acid ester obtained as by-product during step ii) by saponification.

In another embodiment of the present invention, the cosmetic composition of the present invention is flowable at active matter contents of the cosmetic composition higher than 50%, preferably higher than 55% of active weight of the sum of (a), (b) and (d).

In an embodiment of the present invention, the viscosity of the cosmetic composition is lower than 37000 cP (20° C.)

In another embodiment of the present invention, the viscosity of the cosmetic composition is from 12000 to 20000 cP (20° C.).

The cosmetic composition of the present invention may also comprise water.

The pH of the cosmetic composition of the present invention is comprised between 5.5 to 11.4.

Another aspect of the invention is a method to obtain the cosmetic composition of the present invention; said method comprises a step a) of mixing the components with water and a step b) of stirring to obtain a homogeneous solution.

The use of the cosmetic composition of the invention for the cleansing of skin and/or hair is also part of the invention.

In an embodiment of the present invention, the cosmetic composition is used for the cleansing of hair.

In a preferred embodiment of the present invention, the cosmetic composition comprising:

(a) one or more ether carboxylic acid or cosmetically acceptable salt thereof of formula (I)

(b) one or more non-ionic surfactant, wherein the non-ionic surfactant preferably comprises a fatty alcohol;

(c) an amphoteric surfactant

Wherein the molar ratio between the component (a) and (b) is from 8:1 to 2:1, preferably 7:1 to 3:1, more preferably between 6:1 to 4:1;

And wherein the molar ratio between component (a) component (b) and component ((c) is 90:5:5 to 70:5:25, preferably from 70:5:25 to 45:7:48 is used for the cleansing of hair.

In another embodiment of the present invention, the cosmetic composition is used for shaving foams.

In a preferred embodiment of the present invention, the cosmetic composition comprising.

(a) one or more ether carboxylic acid or cosmetically acceptable salt thereof of formula (I)

(b) one or more non-ionic surfactant, wherein the non-ionic surfactant comprises a fatty alcohol;

(c) an amphoteric surfactant

Wherein the molar ratio between the component (a) and (b) is from 8:1 to 2:1, preferably 7:1 to 3:1, more preferably between 6:1 to 4:1;

And wherein the molar ratio between component (a), component (b) and component (c) is from 89:6:5 to 38:15:47, preferably from 82:8:10 to 60:10:30 is used for shaving foams.

A method of cleansing skin and/or hair, wherein the method comprises the steps of wetting or dampening the skin and/or hair, applying a sufficient amount of cosmetic composition according to the invention on the skin and/or hair, and rinsing the skin and/or hair with water.

The cosmetic composition of the present invention can be used in compositions for the cleansing of skin and/or hair, hair dyeing compositions and hair removal compositions. Without being limited by the following list, the skin and hair cleansers comprising the cosmetic composition can be in the form of liquid soaps, shampoos, shaving foams, face cleansers, shower baths, bubble baths, shower or wash gels or creams.

In an embodiment of the present invention, the cosmetic composition is used for the cleansing of skin and/or hair.

In another embodiment, the cosmetic composition is used for hair cleansing. In another embodiment of the present invention, the cosmetic composition is used for skin cleansing. In a further embodiment, the cosmetic composition of the present invention is used in shaving foams.

In another embodiment, the cosmetic composition of the present invention is used for hair dyeing composition. In another embodiment, the cosmetic composition s used in hair removal compositions.

The cosmetic composition according to the present invention may also comprise oil components, silicone compounds, powders, further non-ionic surfactants, anionic surfactants, polymers, metal ion sequestering agents, UV protection factors, vitamins, antioxidants, antioxidant aids, perfume oils, germ inhibitors and the like as further auxiliaries and additives.

Examples of oils include liquid oils, solid oils, waxes, hydrocarbon oils and synthetic ester oils. Suitable oil components are, for example, Guerbet alcohols based on fatty alcohols containing 6 to 22 and preferably 8 to 10 carbon atoms, esters of linear C6-C22 fatty acids with linear C6-C22 fatty alcohols, esters of branched C6-C22 carboxylic acids with linear C6-C22 fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isopropyl myristate, isostearyl palmitate, isostearyl stearate, isostearyl isostearate, isostearyl oleate, isostearyl behenate, isostearyl cleats, oleyl myristate, oleyl palmitate, oleyl stearate, oleyl isostearate, oleyl cleats, oleyl behenate, oleyl erucate, behenyl myristate, behenyl palmitate, behenyl stearate, behenyl isostearate, behenyl cleats, behenyl behenate, behenyl erucate, erucyl myristate, erucyl palmitate, erucyl stearate, erucyl isostearate, erucyl cleats, erucyl behenate and erucyl erucate. Also suitable are esters of linear C6-C22 fatty acids with branched alcohols, more particularly 2-ethyl hexanol, esters of hydroxycarboxylic acids with linear or branched C6-C22 fatty alcohols, esters of linear and/or branched fatty acids with polyhydric alcohols for example propylene glycol, dimer diol or timer trial) and/or Guerbet alcohols, triglycerides based on C6-C10 fatty acids, liquid mono-/di-/triglyceride mixtures based on C6-C18 fatty acids, esters of C6-C22 fatty alcohols and/or Guerbet alcohols with aromatic carboxylic adds, more particularly benzoic acid, esters of C6-C12 dicarboxylic acids with linear or branched alcohols containing 1 to 22 carbon atoms or polyols containing 2 to 10 carbon atoms and 2 to 6 hydroxyl groups, vegetable oils such as avocado oil, almond oil, hazelnut oil, babassu palm oil, borage oil, peanut oil, jojoba oil, canola oil, hemp oil, soybean oil, milk thistle oil, safflower oil, chufa oil, coconut oil, rapeseed oil, black cumin oil, wheat germ oil, sunflower oil, linseed oil, macadamia nut oil, corn oil, walnut oil, olive oil, branched primary alcohols, substituted cyclohexanes, linear and branched C6-C22 fatty alcohol carbonates, Guerbet carbonates, esters of benzoic acid with linear and/or branched C6-C22 alcohols, linear or branched, symmetrical or non-symmetrical dialkyl ethers containing 6 to 22 carbon atoms per alkyl group, ring opening products of epoxidized fatty acid esters with polyols, silicone oils and/or aliphatic or naphthenic hydrocarbons, for example dialkyl cyclohexanes.

Examples of waxes include natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as for example, montan ester waxes, sasol waxes, hydrogenated jojoba waxes and synthetic waxes such as, for example, polyalkylene waxes and polyethylene glycol waxes.

Examples of hydrocarbon oils include liquid paraffin, squalane, pristane, paraffin, ceresin, squalene, petrolatum, and microcrystalline wax.

Suitable silicone compounds are, for example, dimethyl polysiloxanes, methylphenyl polysiloxanes, cyclic silicones and, amino-, fatty acid-, alcohol-, polyether-, epoxy-, fluorine-, glycoside- and/or alkyl-modified silicone compounds which may be both liquid end resin-like at room temperature. Preferred silicone compounds are hydrophobic silicone oils, which are silicone oils which are soluble in paraffinic oil at 25° C. Hydrophobic silicone oils to be used according to the present invention include both volatile and non-volatile silicone oils. Specific examples include a cyclic methyl siloxane having the formula $\{(CH3)2SiO\}_x$ in which x is 3-6, or short chain linear methyl siloxanes having the formula $((CH3)_2SiO\{(CH_3)_2SiO\}_ySi(CH_3)_3$ in which y is 0-5.

Some suitable cyclic methyl siloxanes are hexamethylcyclotrisiloxane (D3), a solid with a boiling point of 134° C. and the formula $\{(Me_2)SiO\}_3$; octamethylcyclotetrasiloxane (D4) with a boiling point of 176° C., a viscosity of 2.3 mm$^2$/s, and the formula $\{(Me_2)SiO\}_4$; decamethylcyclopentasiloxane (D5) (cyclomethicone) with a boiling point of 210° C., a viscosity of 3.87 mm$^2$/s, and the formula $\{(Me_2)SiO\}_5$; and dodecamethylcyclohexasiloxane (DE) with a boiling point of 245° C., a viscosity of 6.62 mm$^2$/s and the formula $\{(Me_2)SiO\}_6$.

Some suitable short linear methyl siloxane are hexamethyldisiloxane (MM) with a boiling point of 100° C., viscosity of 0-65 mm<2>/s, and formula $Me_3SiOMe_3$; octamethyltrisiloxane (MOM) with a boiling point of 152° C., viscosity of 1.04 mm$^2$/s, and formula $Me_3SiOMe_2SiOSiMe_3$; decamethyltetrasiloxane (MD2M) with a boiling point of 194° C., viscosity of 1.53 mm$^2$/s, and formula $Me_3SiO(MeSiO)_2SiMe_3$; dodecamethylpentasiloxane (MD3M) with a boiling point of 229° C., viscosity of 2.06 mm$^2$/s, and formula $Me_3SiO(Me_2SiO)_2SiMe_3$; tetradecamethylhexasiloxane (MD4M) with a boiling point of 245° C., viscosity of 2.63 mm$^2$/s, and formula $Me_3SiO(Me_2SiO)_4SiMe_3$; and hexadecamethylheptasiloxane (MD5M) with a boiling point of 270° C., viscosity of 3.24 mm$^2$/s, and formula $Me_3SiO(Me_2SiO)_5SiMe_3$.

Furthermore, long chain linear siloxanes such as phenyltrimethicone, bis(phenylpropyl)dimethicone, dimethicone, and dimethiconol are also included.

Examples of powders include inorganic powders such as talc, kaolin, mica, sericite, muscovite, phlogopite, synthetic mica, lepidolite, biotite, vermiculite, bentonite, hectorite, laponite, magnesium carbonate, calcium carbonate, aluminum silicate, barium silicate, calcium silicate, magnesium silicate, strontium silicate, tungstate, magnesium, silica, zeolite, barium sulfate, calcined calcium sulfate (calcined gypsum), calcium phosphate, fluorine apatite, hydroxyapatite, ceramic powder, metallic soap (e.g., zinc myristate, calcium palimitate, and aluminum stearate), and boron nitride; organic powders such as polyamide resin powder (nylon powder), polyethylene powder, polymethylmethacrylate powder, polystyrene powder, styrene-acrylic acid copolymer resin powder, benzoguanamine resin powder, poly (tetrafluroethylene) powder, and cellulose powder; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ocher; inorganic black pigments such as black iron oxide and lower order titanium oxide; inorganic purple pigments such as mango violet and cobalt violet; inorganic green pigments such as chrome oxide, chrome hydroxide, and cobalt titanate; inorganic blue pigments such as ultramarine and Prussian blue; pearl pigments such as titanium oxide coated mica, titanium oxide coated bismuth oxychloride, titanium oxide coated talc, colored titanium oxide coated mica, bismuth oxychloride, and fish scale flakes; metal powder pigments such as aluminum powder and copper powder; organic pigments such as zirconium, barium, or aluminum lake (e.g., organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404,or Red No. 3, Red No. 104, Red No. 106, Red No. 227, Red No. 230, Red No. 401, Red No. 505, Orange No. 205. Yellow No. 4, Yellow No. 5, Yellow No. 202, Yellow No. 203, Green No. 3 and Blue No. 1); and natural colors such as chlorophyll and β-carotene.

Examples of lipophilic nonionic surfactants include sorbitan fatty acid esters (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerol or polyglycerol fatty acid esters (such as glycerol mono-cotton seed oil fatty acid ester, glycerol monoerucate, glycerol sesquioleate, glycerol monostearate, glycerol-α, α'-oleate pyroglutamate, and glycerol monostearate malate); propylene glycol fatty acid esters (such as propylene glycol monostearate); hardened castor oil derivatives; and glycerol alkyl ethers.

Examples of hydrophilic nonionic surfactants include POE-sorbitan fatty acid esters (such as POE-sorbitan monooleate, POE-sorbitan monostearate, and POE-sorbitan tetraoleate); POE sorbitol fatty acid esters (such as POE-sorbitol monolaurate, POE-sorbitol monooleate, POE-sorbitol pentaoleate, and POE-sorbitol monostearate); POE-glycerol fatty acid esters (such as POE-monooleates, POE-glycerol monostearate, POE-glycerol monoisostearate, and POE-glycerol triisostearate); POE-fatty acid esters (such as POE-distearate, POE-monodioleate, and ethylene glycol distearate); POE-alkyl ethers (such as POE-lauryl ether, POE-oleyl ether, POE-stearyl ether, POE-behenyl ether, POE-2-octyldodecyl ether, and POE-cholestanol ether); Pluronic type surfactants (such as Pluronic); POE/POP-alkyl ethers (such as POE/POP cetyl ether, POE/POP 2-decyltetradecyl ether, POE/POP monobutyl ether, POE/POP hydrogenated lanolin, and POE/POP glycerol ether); tetra POE/tetra POP-ethylenediamine condensates (such as Tetronic); POE-castor oil or hardened castor oil derivatives (such as POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleate); POE-beeswax lanolin derivatives (such as POE-sorbitol beeswax); alkanolamides (such as coconut oil fatty add diethanolamide, lauric acid monoethanolamide, and fatty add isopropanolamide); POE-propylene glycol fatty acid esters; POE-alkylamines; POE-fatty acid amides; sucrose fatty acid esters; alkylethoxydimethylamine oxides; and trioleyl phosphate. Examples of anionic surfactant, are, for example, alkyl sulphates (such as C6-C22 alkyl sulphates, metal salts of said C6-C22 alkyl sulphates as well as the ammonium salts or the salts of the organic amines with alkyl or hydroxyalkyl substituents), alkyl ether sulfate surfactant type (such as C6-C22 alkyl ether sulphates containing 0.5 to 5, preferably 0.8 to 3, moles of ethylene oxide per mol of the C6-C22 alkyl ether sulphate, metal salts of said alkylC6-C22 ether sulphates as well as the ammonium salts of organic amines with alkyl or hydroxyalkyl substituents, examples are sodium lauryl ether sulphate, potassium lauryl ether sulphate, ammonium lauryl ether sulphate and mono-, di- and triethylethanolamine lauryl ether sulphates containing from 0.8 to 3 moles of ethylene oxide per mole of alkyl ether sulphate, or mixtures thereof). Anionic surfactants of the sulfosuccinate types are also possible examples, including the alkylC6-C22 sulfosuccinates and alkylC6-C22 ether sulfosuccinates, preferably the mono- and di-alkylC6-C22 sulfosuccinates and mono- and di-alkylC6-C22 ether sulfosuccinates containing from 0.5 to 10, preferably from 1 to 5 mot of ethylene oxide per mol of alkyl (eg, mono- or di-alkyl) C6-C22 ether sulfosuccinate, or mixtures thereof, it being possible to use the metal salts of said mono- and di-alkylC6-C22 sulfosuccinates and mono- and di-alkyl C6-C22 ether sulfosuccinates as well as ammonium salts or salts of organic amines with alkyl or hydroxyalkyl substituents.

Suitable cationic polymers are, for example, cationic cellulose derivatives such as, for example, the quaternized hydroxyethyl cellulose obtainable from Amerchol under the name of Polymer JR 400, cationic starch, copolymers of diallyl ammonium salts and acrylamides, quaternized vinyl pyrrolidone/vinyl imidazole polymers such as, for example, Luviquat (BASF), condensation products of polyglycols and amines, quaternized collagen polypeptides such as, for example, Lauryidimonium Hydroxypropyl Hydrolyzed Collagen, quaternized wheat polypeptides, polyethyleneimine, cationic silicone polymers such as, for example, Amodimethicone, copolymers of adipic acid and dimethylaminohydroxypropyl diethylenetriamine (Cartaretine, Sandoz), copolymers of acrylic acid with dimethyl diallyl ammonium chloride, polyquaternium type polymers, polyaminopolyamides and crosslinked water-soluble polymers thereof, cationic chitin derivatives such as, for example, quaternized chitosan, optionally in micro-crystalline distribution, condensation products of dihaloalkyls, for example dibromobutane, with bis-dialkylamines, for example bis-dimethylamino-1,3-propane, cationic guar gum such as, for example, Jaguar CBS, Jaguar C-17, Jaguar C-16 of Celanese, quaternized ammonium salt polymers such as, for example, Mirapol A-15, Mirapol AD-1, Mirapol AZ-1 of Mirapol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl, acetate copolymers, vinyl pyrrolidone/dimethylaminoethyl methacrylate/vinyl caprolactam terpolymers and optionally derivatized cellulose ethers and silicones.

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances: 3-benzylidene camphor or 3-benzylidene norcamphor and derivatives thereof, for example 3-(4-methylbenzylidene)-camphor; 4-aminobenzoic add derivatives, preferably 4-(dimethylamino)-benzoic acid-2-ethylhexyl ester, 4-(dimethylamino)-benzoic acid-2-octyl ester and 4-(dimethylamino)-benzoic acid Amylester; esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene); esters of salicylic acid, preferably salicylic acid-2-ethylhexyl ester, salicylic acid-4-isopropylbenzyl ester, salicylic acid homomethyl ester; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably 4-methoxybenzalmalonic acid di-2-ethylhexyl ester; triazine derivatives such as, for example, 2,4,6-trianilino-(p-carbo-2'-ethyl-1'-hexyloxy)-1,3,5-triazine and Octyl Triazone; propane-1,3-diones such as, for example, 1-(4-tert.butylphenyl)-3-(4T-methoxyphenyl)-propane-1,3-dione; 2-phenylbenzimidazole-5-sulfonic acid and alkali metal, alkaline earth metal, ammonium, alkylammonium, alkanolammonium and glucammonium salts thereof; sulfonic acid derivatives of benzophenones, preferably 2-hydroxy-4-methoxybenzophenone-5-sulfonic acid and salts thereof; sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic add and salts thereof.

Typical UV-A filters are, in particular, derivatives of benzoyl methane such as, for example 1-(4'-tert, butylphenyl)-3-(4'-methoxyphenyl)-propane-1,3-dione, 4-tert-butyl- 4'-methoxydibenzoyl methane (Parsol 1789) or 1-phenyl-3-(4'-isopropylphenyl)-propane-1,3-dione.

The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Titandioxid T 805 (Degussa) or Eusolex T2000 (Merck). Suitable hydrophobic coating materials are, above all, silicones and especially trialkoxyoctyl silanes or simethicones. So-called micro- or nanopigments are preferably used in sun protection products. Micronized zinc oxide is preferably used.

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (also (metal) chelators (for example (α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, (α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, ZnSO4), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Examples of metal ion sequestering agents include 1-hydroxyethane-1,1-diphosphonic acid, 1-hydroxyethane-1,1-diphosphonic acid 4Na salt, disodium edetate, trisodium edetate, tetrasorium edetate, sodium citrate, sodium polyphosphate, sodium metaphosphate, gluconic acid, phosphoric acid, citric acid, ascorbic acid, succinic acid, edetic acid, and trisodium hydroxyethyl ethylenediamine triacetate.

Examples of vitamins include vitamins A, B1, B2, B6, C, and E and the derivatives hereof; pantothenic acid and the derivatives thereof; and biotin.

Examples of antioxidants include tocopherols, dibutylhydroxytoluene, butylhydroxyanisole, and gallic acid esters. Examples of antioxidant aids include phosphoric acid, citric acid, ascorbic acid, maleic acid, malonic acid, succinic acid, lactic acid, fumaric acid, cephalin, hexametaphosphates, phytic acid, and ethylenediaminetetraacetic acid.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert-butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, filial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the farm of mixtures: bergamot oil, dihydromyrcenol, lilial, lyral, citronellol, phenylethyl alcohol, α-nexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascene, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Typical examples of germ inhibitors are preservatives which act specifically against gram-positive bacteria such as, for example, 2,4,4'-trichloro-Z-hydroxydiphenyl ether, chlorhexidine (1,6-di-(4-chlorophenyl-biguanido)-hexane) or TCC (3,4,4'-trichlorocarbanilide), Numerous perfumes and essential oils also have antimicrobial properties. Typical examples are the active substances eugenol, menthol and thymol in clove, mint and thyme oil.

The following examples are given in order to provide a person skilled in the art with a sufficiently clear and complete explanation of the present invention, but should not be considered as limiting of the essential aspects of its subject, as set out in the preceding portions of this description.

EXAMPLES

The first part of the Examples section corresponds to the preparation of the cosmetic compositions according to the invention.

The second part of the Examples section refers to the performance of the cosmetic composition of the present invention.

Example 1

Preparation of Composition A (Comparative)

417 g of ethoxylate (Kalcol 2465+2.5 moles ethylene oxide) were filled into a reactor and heated up to 72° C. under stirring. Then 1.4 g of water was added.

233 g sodium monochloroacetate and 88 g sodium hydroxide were added within 5 hours, so that the temperature was kept at 72±4° C. After finishing of the reaction, the mixture was treated with 800 g water and 243 g hydrochloric acid (30% solution in water) for neutralization at 95° C. Stirring was stopped at 95° C. for phase separation. After 1 hour of separation time the aqueous layer was drained to obtain the ether carboxylic acid (upper layer).

Preparation of Composition B (According to the Invention)

417 g of ethoxylate (Kalcol 2465+2.5 moles ethylene oxide) were filled into a reactor and heated up to 72° C. under stirring. Then 1.4 g of water was added.

233 g sodium monochloroacetate and 88 g sodium hydroxide were added within 5 hours, so that the temperature was kept at 72±4° C. After finishing of the reaction, the mixture was treated with 800 g water and 243 g hydrochloric acid (30% solution in water) for neutralization at 95° C. Stirring was stopped at 95° C. for phase separation. After 1 hour of separation time the aqueous layer was drained to obtain the ether carboxylic acid (upper layer).

336 g water were filled into a reactor; 26.6 g potassium hydroxide (50% solution in water) were added under stirring and the alkaline solution was heated up to 65-70° C. Then 100 g of the above described product were added under stirring. The mixture was stirred at 65-70° C. for 2 hours.

Table 1 summarizes the analytical results for the content of the compositions.

Content of ether carboxylic acid (EC) was determined by the potentiometric analysis Alkali Epton using titrant Hyamine 1622 as cationic organic salt. Samples were dissolved in a mixture of water, methanol and chloroform.

Composition A was saponified to determine, by difference, the content of ether carboxylic acid ester. Content of ester was determined by difference of the Alkali Epton and Alkali Epton after saponification.

Content of nonionic was determined by the difference of theoretical Alkali Epton if reaction was at 100% of conversion and the determined experimental Alkali Epton. Content of non-ionic is obtained by difference with the amount of ether carboxylic acid ester.

Table 1 describes the molar ratio between component (a) and (b) and, the content of ether carboxylic acid ester (d):

TABLE 1

|  | molar ratio (a):(b) | % wt (d) |
|---|---|---|
| Composition A | 30:1 | 15.6 |
| Composition B | 5:1 | 0.6 |

*wt: with respect to the total active weight of the sum of (a), (b) and (d)

Example 2

Performance of the cosmetic compositions prepared in Example is summarized in Table 2 below.

TABLE 2

|  | Foam Consistency [g] | Foam creaminess [1-5] |
|---|---|---|
| Composition A | 3.6 | 3.7 |
| Composition B | 4.8 | 4.3 |

Foam consistency was determined using a Texture Analyzer TA.XTPlus (20 mmØcylinder aluminium probe). The foam was created by manually washing a Caucasian hair tress of approximately 10 g and 22 cm in length with a sample prepared to obtain 4% a.m. concentration and pH=5.5. The tress was washed using tap water of approximately 0° F. of water hardness. The foam created by manually washing the tress was collected in a glass recipient of 45 mmØ and the foam consistency value was obtained at 10 seconds after starting the measurement.

Foam creaminess of the samples was determined by means of a sensorial test carried out by a panel of 6 experts washing Caucasian hair tress of approximately 10 g and 22 cm in length with a sample prepared to obtain a concentration of 1.5% a.m. and pH=5.5. The tress was washed using tap water of approximately 20° F. of water hardness. The sensory score was given with a reference sample and the comparative evaluation was made according to the following criteria:

1: much lower performance than the reference sample
2: lower performance than the reference sample
3: reference sample
4: better performance than the reference sample
5: much better performance than the reference sample Composition according to the invention presents better values regarding foam consistency and foam creaminess.

The invention claimed is:
1. A cosmetic composition comprising:
(a) One or more ether carboxylic acid or cosmetically acceptable salt thereof of formula (I)

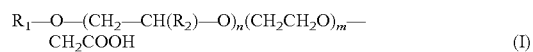

(I)

wherein $R_1$ is a linear or branched alkyl or alkenyl chain having from 4 to 22 carbon atoms;

$R_2$ is a $C_1$-$C_3$ linear or branched alkyl chain, n and m are independently an integer number from 0 to 15, and wherein the sum of m+n is from 1 to 15;

(b) a non-ionic surfactant comprising a fatty alcohol of formula (III)

$$R_3-O-(CH_2-CH(R_4)O)_p-(CH_2CH_2O)_q-H \quad \text{Formula (III)}$$

wherein $R_3$ is a linear or branched alkyl chain, having from 4 to 22 carbon atoms; $R_4$ is a $C_1$-$C_3$ linear or branched alkyl chain, p and q are independently an integer number from 0 to 15, and wherein the sum of p+q is from 0 to 15;

wherein the composition is essentially absent in a component (d) which is a fatty acid ester of formula (IV)

$$R_1-O-(CH_2-CH(R_2)-O)_n(CH_2CH_2O)_m-CH_2COOR_5 \quad \text{(IV)}$$

wherein $R_1$ is an alkyl or alkenyl chain having from 4 to 22 carbon atoms; $R_2$ is a $C_1$-$C_3$ linear or branched alkyl chain, $R_5$ is an alkyl or alkenyl chain, having from 4 to 22 carbon atoms, or $-(CH_2-CH(R_2)-O)_p(CH_2CH_2O)_q-R_3$; wherein $R_3$ is an alkyl or alkenyl chain, having from 4 to 22 carbon atoms, n and m are independently an integer number from 0 to 15, the sum of n+m is from 1 to 15; p and q are independently an integer number from 0 to 15, the sum of p+q is from 1 to 15; and wherein the amount of (d) is lower than 2% wt with respect to the total active weight of the sum of (a), (b) and (d); and wherein the molar ratio between the component (a) and (b) is from 8:1 to 2:1.

2. A cosmetic composition according to claim 1, characterized in that the composition further comprises (c) an amphoteric surfactant.

3. A cosmetic composition according to claim 1, characterized in that the composition further comprises a component (e) being an electrolyte.

4. A cosmetic composition according to claim 1, characterized in that the percentage of active matter comprising at least (a) an ether carboxylic acid or salt thereof of formula (I), and (b) a non-ionic surfactant is higher than 50% of the cosmetic composition.

5. A cosmetic composition comprising:
(a) One or more ether carboxylic acid or a cosmetically acceptable salt thereof of formula (I)

$$R_1-O-(CH_2-CH(R_2)-O)_n(CH_2CH_2O)_m-CH_2COOH \quad \text{(I)}$$

wherein $R_1$ is a linear or branched alkyl or alkenyl chain having from 4 to 22 carbon atoms;

$R_2$ is a $C_1$-$C_3$ linear or branched alkyl chain, n and m are independently an integer number from 0 to 15, and wherein the sum of m+n is from 1 to 15;

(b) a non-ionic surfactant wherein the molar ratio between the component (a) and (b) is from 8:1 to 2:1; and wherein the composition is obtainable by a process comprising at least the following steps:
i. Alkoxylating a fatty alcohol
ii. Carboxymethylating the mixture obtained in step i) comprising at least an alkoxylated alcohol and alkoxides thereof with a $C_2$ to $C_5$ chlorocarboxylic acid;
iii. Hydrolysis of the ether carboxylic acid ester obtained as by-product during step ii) by saponification reaction; and wherein the composition is essentially absent in a component (d) which is a fatty acid ester of formula (IV)

$$R_1-O-(CH_2-CH(R_2)-O)_n(CH_2CH_2O)_m-CH_2COOR_5 \quad \text{(IV)}$$

wherein $R_1$ is an alkyl or alkenyl chain having from 4 to 22 carbon atoms; $R_2$ is a $C_1$-$C_3$ linear or branched alkyl chain, $R_5$ is an alkyl or alkenyl chain, having from 4 to 22 carbon atoms or $-(CH_2-CH(R_2)-O)_p(CH_2CH_2O)_q-R_3$; wherein $R_3$ is an alkyl or alkenyl chain, having from 4 to 22 carbon atoms, n and m are independently an integer number from 0 to 15, the sum of n+m is from 1 to 15; p and q are independently an integer number from 0 to 15, the sum of p+q is from 0 to 15;

wherein the amount of (d) is lower than 2% wt with respect to the total active weight of the sum of (a), (b) and (d).

6. A cosmetic composition according to claim 5, characterized in that the composition further comprises (c) an amphoteric surfactant.

7. A cosmetic composition according to claim 5, characterized in that the percentage of active matter comprising at least (a) an ether carboxylic acid or salt thereof of formula (I), and (b) is higher than 50% of the cosmetic composition.

8. A cosmetic composition according to claim 2, wherein the cosmetic composition comprises:
between 27% and 90% of component (a);
between 3% and 15% of component (b); and
between 5% and 70% of component (c);
each of the indicated amounts being expressed as percentage by weight of the mentioned component with respect to the total active weight of the sum of (a), (b) and (c).

9. A cosmetic composition according to claim 6, wherein the cosmetic composition comprises:
between 27% and 90% of component (a);
between 3% and 15% of component (b); and
between 5% and 70% of component (c);
each of the indicated amounts being expressed as percentage by weight of the mentioned component with respect to the total active weight of the sum of (a), (b) and (c).

10. The cosmetic composition of claim 1, wherein the amount of component (d) is lower than 1% wt. with respect to the total active weight of the sum of (a), (b) and (d).

11. The cosmetic composition of claim 5, wherein the amount of component (d) is lower than 1% wt. with respect to the total active weight of the sum of (a), (b) and (d).

12. A method to prepare a cosmetic composition according to claim 1, comprising the steps:
i. mixing the components with water;
ii. stirring to obtain a homogeneous solution.

13. A method to cleanse skin and/or hair comprising the steps of wetting or dampening the skin and/or hair, applying a sufficient amount of the composition according to claim 1 on the skin and/or hair, followed by rinsing.

* * * * *